United States Patent [19]

Cerami et al.

[11] Patent Number: 4,731,323

[45] Date of Patent: Mar. 15, 1988

[54] METHODS OF MEASUREMENT AND DETECTION EMPLOYING PHOTOSENSITIVE COMPOSITIONS AND PRODUCTS

[75] Inventors: Anthony Cerami, Flanders, N.J.; Michael A. Yamin, New York, N.Y.

[73] Assignee: Evreka, Inc., New York, N.Y.

[21] Appl. No.: 641,082

[22] Filed: Aug. 15, 1984

Related U.S. Application Data

[62] Division of Ser. No. 348,113, Feb. 11, 1982, Pat. No. 4,466,941.

[51] Int. Cl.[4] .......................... C12Q 1/00; C12Q 1/32; C12M 1/34

[52] U.S. Cl. .......................................... 435/4; 435/291; 435/808; 435/26

[58] Field of Search .................... 436/164, 169; 435/4, 435/26, 291, 808, 10–12, 14–17, 805, 810

[56] References Cited

U.S. PATENT DOCUMENTS

| | | | |
|---|---|---|---|
| 1,845,835 | 2/1932 | Frankenburger et al. . | |
| 2,325,038 | 7/1943 | Chalkley | 260/387 |
| 2,366,179 | 1/1945 | Chalkley | 260/391 |
| 2,441,561 | 5/1948 | Chalkley | 204/158 |
| 2,528,496 | 11/1950 | Chalkley | 95/7 |
| 2,676,887 | 4/1954 | Chalkley | 95/7 |
| 2,829,052 | 4/1958 | Chalkley . | |
| 2,829,148 | 4/1958 | Chalkley | 260/391 |
| 2,829,149 | 4/1958 | Chalkley . | |
| 2,839,542 | 6/1958 | Chalkley | 260/391 |
| 2,839,543 | 6/1958 | Chalkley | 260/394 |
| 2,844,465 | 7/1958 | Chalkley | 96/48 |
| 2,855,303 | 10/1958 | Chalkley | 430/338 X |
| 2,855,304 | 10/1958 | Chalkley | 96/90 |
| 2,877,166 | 3/1959 | Chalkley | 204/158 |
| 2,877,167 | 3/1959 | Chalkley | 204/158 |
| 2,877,168 | 3/1959 | Chalkley | 204/158 |
| 2,877,169 | 3/1959 | Chalkley | 204/158 |
| 2,895,892 | 7/1959 | Chalkley . | |
| 2,936,235 | 5/1960 | Chalkley . | |
| 2,936,276 | 5/1960 | Chalkley | 204/158 |
| 3,071,464 | 1/1963 | Chalkley | 96/27 |
| 3,122,438 | 2/1964 | Chalkley | 96/90 |
| 3,236,648 | 2/1966 | Chalkley | 96/48 |
| 3,382,074 | 5/1968 | Kimura et al. . | |
| 3,407,065 | 10/1968 | Chalkley | 96/33 |
| 3,837,746 | 9/1974 | Acker et al. | 435/291 X |
| 3,881,992 | 5/1975 | Ralston | 436/164 X |
| 4,062,713 | 12/1977 | Anderson | 156/256 |
| 4,379,840 | 4/1983 | Gorka et al. | 435/10 |
| 4,466,941 | 8/1984 | Cerami et al. | 260/390 X |

OTHER PUBLICATIONS

Chalkley, L., Photometric Papers Sensitive Only to Short Wave Ultraviolet, Journal of the Optical Society of America 42(6):387–392 (1952).

Chalkley, L., Organic Mercury Derivatives of Basic Triarylmethane Dyes: Dimercuri Derivatives of Malachite Green, J.A.C.S. 63:981–987 (1941).

Miyake, Y., A New Chemical Method for Measuring the Ultra-Violet Ray, Bulletin of the Chemical Society of Japan 22:105–109 (1949).

Harris, L., et al. The Absorption Spectrum of Malachite Green Leucocyanide and the Mechanism of the Dark Reaction After Photolysis, J.A.C.S. 57:1151–1154 (1935).

Harris, L. et al. A Precision Actinometer for the Ultraviolet Region (including an exact text of the Einstein Equivalence Law), J.A.C.S. 57:1154–1159, (1935).

Zweig, A., et al. A Photochemical Mid-Ultraviolet Dosimeter for Practical Use as a Sunburn Dosimeter, Photochemistry and Photobiology 24:543–549 (1976).

Weyde, E., et al. The Measurement of Ultraviolet Radiation, Especially of the Physiologically Active Ultraviolet (which produces erythema), by Means of the Photochemical Formation of Triphenylmethane Dyes from the Leuco Compounds, Transactions of the Faraday Society 27:561–571, Plus Discussion (1931).

Chalkley, L., The Mercuration of Methylene Blue, J.A.C.S. 47:2055–2061 (1925).

Calvert, J. G., et al. Precision Actinometry at Low Light Intensities with Malachite Green Leucocyanide, J.A.C.S. 74:2101–2103 (1952).

*Primary Examiner*—Robert J. Warden
*Assistant Examiner*—Randall E. Deck
*Attorney, Agent, or Firm*—Popper, Bobis & Jackson

[57] ABSTRACT

The present invention relates to methods for measurement and detection which employ a photosensitive indicator which may be prepared from a composition capable of offering a visual, calibrated reaction to the presence of ultraviolet radiation. The indicator preferably employs a composition comprising a complex of a leuco dye and animal-derived serum albumin. The leuco dye-serum albumin complex is capable of exacting calibration, so that scientifically significant quantitative measurements of radiation falling within the wavelengths of ultraviolet light and lower may be made. Numerous techniques useful in a variety of diagnostic applications are made possible, including the measurement of bioactive materials that are independently capable of absorbing ultraviolet wave energy, as well as bioactive materials that by association with certain ancillary materials capable of modulating their ultraviolet light absorption may similarly be quantitatively measured.

10 Claims, No Drawings

METHODS OF MEASUREMENT AND DETECTION EMPLOYING PHOTOSENSITIVE COMPOSITIONS AND PRODUCTS

This is a division of application Ser. No. 348,113, filed Feb. 11, 1982, now U.S. Pat. No. 4,466,941, issued Aug. 21, 1984.

BACKGROUND OF THE INVENTION

1. Field of the Invention the present invention relates generally to photosensitive materials, and particularly to those materials sensitive to exposure to ultraviolet light.

2. Description of the Prior Art

Photosensitive compositions for the detection and indication of ultraviolet light are well known. More particularly, a series of U.S. Patents held by Lyman Chalkley discusses a system utilizing certain photosensitive substances identified as leuco-cyanides of aminotriarylmethane dyes. Chalkley conducted indepth investigations with these dyes, and proposed a series of compositions, containing the leuco-cyanide dyes, with various activators, such as carboxylic acids, amides, mercurous derivatives and silver derivatives. In other instances, Chalkley proposed to heat the dye-cyanide complex together with its activator, to a point of fusion, at which exposure to ultraviolet radiation was made. The foregoing and other variations on this investigation are set forth in U.S. Patents, and a partial listing is provided herein. U.S. Pat. Nos. 2,325,038; 2,366,179; 2,441,561; 2,528,496; 2,676,887; 2,829,052; 2,829,148; 2,839,542; 2,839,543; 2,844,465; 2,855,303; 2,855,304; 2,877,166; 2,936,235; 3,122,438; and 3,407,065; are referred to as representative.

A full review of the Chalkley publications, and other publications relating to this subject, indicated that the leuco-cyanides exhibited certain inadequacies in operation, that rendered them incapable of general acceptance for the purposes of detecting and quantifying ultraviolet radiation with scientific accuracy. In particular, the leuco-cyanides, regardless of their specific composition, all appeared to require the presence of an activator compound for their operation. Without this activation compound, either the leuco-cyanides would not give the color reaction expected upon exposure to ultraviolet radiation, or would give such color reaction and later exhibit loss of intensity and fading. In either event, the instability of the leuco-cyanide dye system rendered it unreliable for widespread acceptance and use.

The measurement of electromagnetic wave energy, in the area of x-rays, gamma rays and ultraviolet light has become increasingly important, from the standpoint of thereoretical scientific investigation, as well as practical attention to personal health. It is therefore important to be able to quantitatively delineate radiation in this portion of the spectrum with speed and precision, and a need therefore exists for a system that can be inexpensively and easily used in a scientifically reproducible, and therefore reliable manner.

SUMMARY OF THE INVENTION

In accordance with the present invention, a composition and related indicator product are disclosed, which are capable of offering a visual, calibrated reaction to the presence of ultraviolet radiation. The composition, in its simplest aspect, comprises a complex of leuco-cyanide and animal-derived serum albumin. The complex is preferably preferred in a molar ratio of leuco-cyanide to serum albumin, of from about 1:1 to about 6:1. Preferably, the leuco-cyanides comprise the cyanides of aminotriarylmethane dyes, such as pararosaniline, rosaniline, malachite green, acid fuchsin, and the like. The composition preferably includes a material capable of binding the complex to a substrate. The material preferably is one capable of forming either a covalent bond with proteins, or one having a hydrophobic moiety as part thereof. Suitable binding materials, may include, for example, a copolymer of maleic anhydride and methyl vinyl ether.

The present invention also includes an indicator for detection and measurement of ultraviolet radiation, comprising the leuco-cyanide-serum albumin complex, adhesively disposed upon a substrate. In particular, the adhesive or binder material may comprise one of the class of materials set forth above, and the substrate may be selected from insoluble, hydrophilic materials, such as vinyl polymers, cellulose derivatives, film-forming carbohydrates, and others. Preferably, the indicator may be prepared with the substrate having a coating of the binding material disposed initially thereon, a quantity of the complex disposed thereover, and a top coat comprising a material transmissive to ultraviolet radiation, such as polyacrylic acid.

The present invention further includes a method for preparing the complex of the leuco-cyanide and the animal-derived serum albumin, comprising reacting the aminotriarylmethane dye with a cyanide salt in accordance with known procedures, to form the leuco-cyanide, thereafter reacting the leuco-cyanide with a quantity of serum albumin at a mildly acidic pH, by forming a solution thereof. The indicator may thereafter be prepared, by initially disposing the binder material on the selected substrate, and, subsequent to evaporate drying of the binder material, disposing a quantity of the complex thereover, after which the top coat may be applied, such as by spraying or printing.

In an alternate embodiment, the complex and the binder may be simultaneously applied in the substrate by a printing operation, and the top coat may thereafter be applied by a similar technique.

The complex and indicator of the present invention offer precise detection and measurement of ultraviolet radiation, that renders them particularly useful in a variety of applications. For example, the indicator may be prepared with a quantity of a sunscreen such as para-aminobenzoic acid (PABA) to serve as a sun exposure meter. In such instance, the amount of sunscreen would be added in predetermined amounts, to establish a continuum of exposure times, to aid the individual wishing to develop a suntan on a graduated basis. The complex and indicator of the present invention possess possible utility in the preparation of an instant developing x-ray film. Also, in other areas and applications where ultraviolet radiation is monitored, such as in the field of dermatology and in analytical techniques utilized with protein chemistry, instantaneous and accurate identifications and measurements may be possible, that would supplant existing, more time-consuming techniques.

The present invention is particularly notewaorthy,, as it eliminates the need for the addition of activator compounds to the leuco-cyanide, and therefore provides a non-toxic and reliable system having great scientific and personal health care potential.

Accordingly, it is a principal object of the present invention to provide a composition for the identification and measurement of ultraviolet radiation.

It is a further object of the present invention to provide a composition and indicator as aforesaid, that utilizes a leuco-cyanide of aminotriarylmethane dyes, in a simplified yet reliable manner.

It is a further object of the present invention to provide a composition and indicator as aforesaid, that eliminates the need for activation and standarization by application of volatile compounds or rigorous processing.

It is a yet further object of the present invention to provide a composition and indicator as aforesaid having broad utility in clinical, experimental and personal health care applications.

Other objects and advantages will become apparent to those skilled in the art from a consideration of the ensuring detailed description.

DETAILED DESCRIPTION

The present invention relates to a composition for the detection and measurement of ultraviolet radiation. The composition is applicable for the detection of x-rays, gamma rays and other short wavelength radiation, none of which reside within the visible range. The present invention endeavors to utilize the utilty that has been recognized with respect to aminotriarylmethane dyes. A listing of these dyes can be found in H. J. Conn, *Biological Stains* (1971) ed. R. D. Lillie, Williams & Wilkins Co., Baltimore, Md. These dyes can be reacted with various compounds (e.g. cyanide and bisulfite compounds) to form compounds known as leuco dyes. Such leuco dyes are also well recognized in the various patents and other publications to Chalkley, referred to earlier herein and incorporated herein by reference.

As noted earlier, these leuco dyes, while specific in their capability to react ot ultraviolet radiation, have proved unstable and therefore unreliable in previous efforts at application. In particular, the Chalkley patents provide that an activating compound must generally be present in the instance where these leuco dyes are utilized to detect ultraviolet radiation.

The present composition includes the preparation of a complex of these leuco dyes or leuco-cyanides, with animal-derived serum albumin. This form of protein is naturally occurring. The binding sites for hydrophobic compounds that are present on the serum albumin of the invention, allow an aqueous solution to be prepared from an otherwise water-insoluble leuco-cyanide.

A variety of leuco-cyanides are useful in accordance with the present invention. In particular, hydrophobic leuco-cyanides are preferred, and comprise the dyes known as crystal violet, malachite green, rosaniline, pararosaniline, brilliant green, new fuchsine, and others. These dyes are all generically identified as aminotriarylmethane dyes, and specific reference to the text by H. J. Conn, referred to earlier and incorporated herein by reference, may be made for other dyes suitable in accordance with the present invention.

The leuco-cyanides may be prepared by techniques known in the art, and disclosed in U.S. Pat. No. 2,839,543 to Chalkley, the disclosure of which is incorporated herein by reference. For example, a quantity of the aminotriarylmethane dye is placed in an aqueous solution, and heated in a sealed tube together with a quantity of a cyanide salt, such as sodium cyanide, for approximately one hour. After cooling, the tube is opened and slightly acidified to liberate unreacted cyanide. As the leuco-cyanide are insoluble in water, the reaction product may be washed with water to free any unreacted dye, and the desired end product may then be recovered.

Naturally, the foregoing technique is one of several known in the art for the preparation of leuco-cyanides, and the invention is accordingly not limited to the specific method of such preparation, but rather encompasses other, alternate methods within its scope.

Thereafter, the animal-derived serum albumin may be combined with the leuco-cyanide and reacted to from the complex of the present invention. A viable technique for this reaction, comprises the formation of a solution of the leuco-cyanide within a solvent such as ethanol or dimethyl sulfoxide, and the introduction of this solution to a solution of serum albumin. The respective components of the complex may be combined in a variety of ratios, extending for example, from a molar ratio of leuco-cyanide to albumin, of from 1:1 to about 6:1.

A feature of the complex of the present invention, is that the leuco-cyanide is held to the serum albumin by specific hydrophobic bonds which thereby resist breakdown and provide stability to the complex when it is exposed to ultraviolet radiation. In addition, the present complex may be prepared and will operate successfully with certain cationic dyes, as well, and this constitutes an added feature of the present invention.

The composition also includes a material capable of binding the complex to a substrate, in a manner that is irreversible and stable. This finds utility in the instance where it is desired to define the locus of radiation on a molecular level, as the albumin is capable of covalently binding to a variety of substrates. The employment of the binders of the present invention fixes the complex in an exact spatial configuration.

Accordingly, numerous binding materials are useful to affix the serum albumin to various substrates, and include certain water-insoluble resins, and more particularly those materials capable of reacting with the hydroxyl, sulfhydryl, carboxyl, and amino groups of the albumin. Useful materials in this regard, include a copolymer of maleic anhydride and methyl vinyl ether, either as such, or with the inclusion of a further hydrophobic moiety, such as poly (n-octadecyl vinyl ether) or polystyrene.

Other materials generally capable of serving as binding materials, comprise polymeric materials having functional groups such as isocyanates, diazonium salts, and others that are capable of reacting with proteins to form covalent links between the albumin and the substrate. Representative binding materials also include bivalent or polyvalent binding materials such as cyanogen bromide, carbodiimides, p,p'-difluoro-m,m'-dinitrodiphenylsulphone, glutaraldehyde, dimethyadipimate, and others.

Other binding materials having functional groups such as mercury derivatives, halogenated ketones and others would be useful, as they are capable of reacting with the individual sulfhydryl groups disposed on each molecule of the complex. The choice of a particular binding material to associate a substrate with the present complex, permits one to carefully differentiate the reactivity of the resulting indicator, to meet specific conditions or requirements attending the investigation of a particular wavelength of ultraviolet radiation. Likewise, the particular stoichiometry of the leuco-cyanide-serum albumin complex on specific substrates, assures quality control and uniformity when quantities of the indicator, described hereinafter, are prepared, so that quantitative measurements can be made reliably over time.

A variety of substrates may be utilized in conjunction with the composition of the present invention, to affix the composition securely thereto. More particularly, the substrates desirably comprise insoluble, hydrophilic materials, and in particular the film-forming materials possessing functional groups selected from the group consisting of hydroxyl groups, amino groups and mixtures thereof. For example, carbohydrate materials such as cross-linked dextrans and agarose, offering hydroxyl groups, or polyamides such as nylon, offering amino groups, can be utilized in film, block, or other three-dimensional configurations, to accept the present composition. Other hydrophilic materials that would be included, would comprise cellulose derivatives, including cellulose ethers and esters, suitable vinyl polymers, including polyvinyl acetate, and polyvinyl alcohol, polyolefins, and others. Thus, the appropriate substrate may range from conventional filter papers, to photographic paper and translucent film, the specific substrate utilized naturally depending upon the intended application of the resulting indicator.

The indicator of the present invention accordingly comprises the composition thereof bound to the substrate by means of the binder material disposed covalently between the substrate and the complex. More particularly, the present indicator may be prepared by first disposing the binder material upon a surface of the substrate, and allowing the binder material to dry. For example, the copolymer of maleic anhydride and methyl vinyl ether may be disposed in an appropriate organic solvent, such as acetone, and thereafter applied to the substrate. The coated substrate may then be permitted to dry, and the acetone to evaporate from the binder material coating.

Thereafter, a quantity of the complex may be applied to the coated surface of the substrate, and the resulting coated substrate allowed to dry further, so that the water is evaporated off.

After the evaporation of the water from the aqueous solution of the complex is complete, the resulting coated substrate may be finally coated by the application of a top coat thereto, for the purpose of sealing the surface. Suitable top coat materials would include those non-toxic materials that are transmissive to ultraviolet radiation within the specific wavelengths sought to be measured by the particular indicator under preparation. For example, an indicator for measuring ultraviolet radiation from exposure to sunlight, could utilize a top coat of acrylic acid or its polymers. The top coat could be applied by a variety of well known techniques, including roller coating and spraying, and the invention is not limited to a specific method of application.

An alternate method is contemplated, wherein the composition including the complex and the binder material may be mixed and applied simultaneously to a substrtate, as by a printing operation. Thereafter, the top coat may be similarly printed to complete the preparation of the indicator in essentially two steps. This approach lends itself to automated manufacturing techniques.

As noted earlier, the exact amounts and proportions of the respective components of the indicator and the composition, will vary, depending upon intended end use. The present invention therefore encompasses a variety of proportions of the respective components of the indicator and composition, within its spirit and scope.

In a particular application, mentioned earlier, and indicator may be prepared for use in determining the amount of ultraviolet radiation received by exposure to the sun. For example, a series of such indicators may be prepared, each indicator calibrated to reflect the reception of a differential amount of ultraviolet light. Thus, an indicator may be prepared as described earlier, with the addition of a predetermined quantity of a sunscreen agent or other ultraviolet absorbing material, to provide a specific increment of ultraviolet exposure by slowing the rate of color development of the indicator. The sunscreen agent may be added directly to either the complex or the top coat, or may be applied as a separate coating between the two. Suitable sunscreen agents include para-aminobenzoic acid (PABA), picric acid, oxybenzone, polystyrene, and others. The exact sunscreen agent to be used is not critical, and can vary within the scope of the present invention.

Again, the serum albumin used herein, is capable of binding these various water-insoluble compounds to form a water-soluble solution that can be printed or otherwise added to the prepared substrate, to provide a system for detecting ultraviolet radiation.

A better understanding of the principles of the present invention will be gained from a consideration of the following illustrative examples.

EXAMPLE I

Several leuco-cyanide-serum albumin complexes were prepared in accordance with the present invention, utilizing the aminotriarylmethane dyes identified as pararosaniline and crystal violet. Batches of leucocyanide were respectively prepared from each of these dyes, by placing each dye in an aqueous solution containing five grams of the dye and two grams of sodium cyanide in fifty milliliters of water. Both solutions were placed in separate sealed tubes, and were then heated at 100° C. for sixty minutes. Thereafter, teh containers holding the dye-cyanide reaction products were slowly cooled to room temperature and thereafter opened and the contents acidified to liberate unreacted cyanide. The precipitates in each tube were thereafter washed with water to remove any unreacted dye, and the leucocyanide dyes were then recovered.

The complexes between the leuco-cyanides and a quantity of serum albumin were then prepared, by dissolving a quantity of the cyanide in dimethyl sulfoxide, and slowly adding this resulting solution to a solution of non-defatted bovine serum albumin, maintained at a pH of 6.0. The dye component was immediately soluble in the albumin solution, and the complex was promptly formed.

The resulting complexes prepared with each of the respective dyes, were then available for either independent use as a photosensor, or further processing to bind with a suitable substrate.

EXAMPLE II

The complexes prepared in Example I, above, were bound to a quantity of Whatman No. 1 filter paper by the following technique. Several 6.0 mm circular pieces of filter paper were saturated with 7.5 μl quantities of an acetone solution containing 1.0% (w/v) of a copolymer of maleic anhydride and methyl vinyl ether. After the acetone had evaporated from each of the filter papers so treated, 7.5 μl portions of each of the complexes prepared in Example I, above, were added to respective paper samples. In each instance, the excess water from the solution of the complexes was permitted to evaporate, and a coating of acrylic acid was thereafter applied over the complexes by spraying. After the top coat of acrylic acid was dry, the respective filter paper indicator samples were ready for exposure.

The exposure of the respective white paper samples to ultraviolet light at less than 320 mμ were conducted, and in the instance of the complex containing pararosaniline, a deep magenta color developed. In the instance of the complex having crystal violet leuco-cyanide, a blue color resulted.

EXAMPLE III

A series of sunlight indicators were prepared, following the procedures outlined in Examples I and II, above. Thus, a quantity of a complex between pararosaniline cyanide and serum albumin was prepared in accordance with Example I. Several Whatman No. 1 filter papers were prepared with a binder of the maleic anhydride copolymer utilized in Example II, and were thereafter coated with respective quantities of the leuco-cyanide-albumin complex. Thereafter, individual indicator specimens were coated, respectively, with 7.5 μl (100 mg/ml) solutions of para-aminobenzoic acid (PABA) ranging in percent of solution from 0.05% to 0.25% PABA. One of the indicators was prepared without the application of PABA, and each of the indicators were completed with a top coat of polyacrylic acid.

After preparation of the indicators was complete, the indicators were exposed to an ultraviolet sunlamp manufactured by Sylvania having a 275 watt output, at a distance of 36 inches from the light source. Measurements were taken of the time that elapsed from initial exposure, until the respective indicators gave a full color reaction. The results of these tests are set forth in Table I, below.

TABLE I

| INDICATOR # | % PABA APPLIED | FULL EXPOSURE TIME (MINUTES) |
|---|---|---|
| 1 | None | 4 minutes |
| 2 | 0.5% | 5.5 minutes |
| 3 | .10% | 7.5 minutes |
| 4 | .15% | 10 minutes |
| 5 | .25% | 12 minutes |

From this prelminary test, it was apparent that a graded response could be achieved by the predetermined addition of a quantity of sunscreen to quantitatively identify the amount of ultraviolet light.

EXAMPLE IV

Additional indicators were prepared following the procedures of the previous Examples, with the exception that the PABA solution was added directly to the leuco-cyanide-albumin complex, prior to its application to the filter paper substrates. The prepared indicators were thereafter exposed to actual sunlight, with the following results, set forth in Table II, below.

TABLE II

| INDICATOR # | % PABA INCLUDED WITH COMPLEX | FULL EXPOSURE TIME (MINUTES) |
|---|---|---|
| 6 | 0 | 1-2 minutes |
| 7 | .91% | 10-20 minutes |

TABLE II-continued

| INDICATOR # | % PABA INCLUDED WITH COMPLEX | FULL EXPOSURE TIME (MINUTES) |
|---|---|---|
| 8 | 1.8% | 22-26 minutes |
| 9 | 3.3% | 90 minutes |
| 10 | 5.2% | 158 minutes |

The increased quantities of PABA were added to account for the increased intensity of radiation expected with actual sunlight to change the color. From the above test, it was preliminarily determined that a linear relationship exists between the quantity of PABA sunscreen added, and the increments of time extension accorded to the indicator. With respect to Samples 6-10, it was determined that an inclusion of approximately 0.36% PABA resulted in an increment of time extension, of approximately one minute. It appears therefore possible to achieve careful linear calibration of a sunlight meter utilizing the indicator of the present invention and specified quantities of sunscreen.

As noted earlier, the composition and indicator of the present invention has a broad based utility in both personal health care and pure scientific application. For example, a medical application of the present invention resides in the field of dermatology, where patients are exposed to therapeutic amounts of ultraviolet light for various skin disorders, such as psoriasis and skin cancer, where specified amounts of ultraviolet light are prescribed and should not be exceeded. Likewise, the present indicator could be utilized to measure the quantity of ultraviolet light exposure given to hospital rooms and equipment, for purposes of sterilization, to determine that such exposure is sufficient in both time and dosage to achieve the desired sterilization.

A further application resides in the field of biochemistry, where the fixation of the complex to a substrate with a particular stoichiometry and position, would permit the exacting definition of the presence and position of individual protein and nucleic acids present in tissue and fluid specimens. Thus, for example, conventinal gel electrophoresis staining techniques that are utilized, could be dispensed with and the sample containing the biopolymers could be placed over an indicator specially prepared in accordance with the present invention, in which instance exposure to ultraviolet light would result in the development of a uniform color on the indicator with the exception of those regions where the biopolymer was present, since these materials absorb ultraviolet light. As the specific wavelengths under investigation could be accommodated by the preparation of a particular indicator, individual biopolymers could be identified rapidly and accurately without the destructive consequences of conventional techniques.

The present indicator and composition are also useful in the area of photography, and in particular, in the area of x-ray photography. Conventinal x-rays require substantial time for development, which could be rendered unnecessary by the employment of a film backing utilizing the structure of the present indicator. The resulting x-ray film would be virtually instantaneous in development and would require no processing. In such instance, the exposed indicators or films could be preserved by placement in ultraviolet light-excluding pouches or folders.

Another application contemplates using the present indicators as a means for quantifying radioactivity. For example, a solvent such as toluene could be raised to an excited state, by exposure to gamma rays or beta particles. In this excited state, the solvent would produce ultraviolet light that could be absorbed by and indicator with a resulting change in color. The amount of the color change could then be monitored by a conventional spectrophotometer, and the amount of radiation would thus be determined.

A further and important application for the indicator of the present invention, is in the area of clinical strips that would measure the presence and amount of important biological enzymes and substrates. These substrates are useful in determining the clinical status of humans and animals. At present, many of the available clinical tests are not adaptable to performance with test strips, as they utilize the interconversion of Nicotinamide Adenine Dinucleotide Phosphate, NAD(P) and the reduced form of NAD(P) identified as NAD(P)H, as a spectrophotometric measure of enzyme activity. This is due to efforts to take advantage of the fact that NAD(P)H absorbs light at 320 m$\mu$. This wavelength is at the border of the visible spectrum, and has therefore been difficult for eye discrimination. By carrying out reactions in appropriate containers that will permit light at this wavelength to reach a photosensitive element such as the indicator of the present invention, a faint color could be converted to a clearly visible color, which could then be quantitatively measured by comparison, or by the technique of reflectometry.

The number of potential enzymes and substrates that would be capable of measurement with this technique, would include by example the following: alanine aminotransferase; ethyl alcohol; ammonia; creatine phospholinase; 2,3-diphosphoglyceric acid; formamino-L-glutamic acid; galactose-1-phosphate uridyl transferase; glucose; glucose-6-phosphate dehydrogenase; lactate dehydrogenase; serum glutamic oxaloacetic transaminase; serum glutamic pyruvic transaminase; triglycerides; urea nitrogen; uric acid; vanilmandelic acid.

It should be apparent from the foregoing discussion, that the indicator and composition of the present invention possess a broad interdisciplinary spectrum of utility, that requires only further investigation and adaptation to further fulfill.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

What is claimed is:

1. A method for measuring the presence of bioactive materials known to absorb ultraviolet light energy comprising:

A. disposing a quantity of a medium suspected of containing at least one of said bioactive materials in a container transmissive to ultraviolet light energy;

B. locating said container in the path of a beam of ultraviolet light energy emitted from a source therefor;

C. locating an indicator sensitive to said light energy beam in operative position adjacent said container and in the path of said light energy beam to receive any of the light energy of said beam that may pass therethrough, said indicator comprising a water and solvent-insoluble substrate on which is disposed a quantity of a photosensitive composition consisting essentially of a complex of a hydrophobic leuco dye and animal-derived serum albumin, said leuco dye and said serum albumin are bound to each other in said complex by hydrophobic bonds;

D. activating said light energy source to direct said beam against said container; and E. determining the presence of said bioactive materials by inspecting said indicator after said beam has been directed against said container to measure the presence and amount of any of said light energy absorbed by said indicator, wherein the absence of a color reaction on said indicator reveals the presence of said bioactive materials.

2. The method of claim 1 wherein bioactive materials that are present, are disposed in fixed position with said medium, and wherein said method further comprises indentifying the location of said bioactive materials within said medium.

3. The method of claim 2 wherein said bioactive materials absorb light at different wavelengths.

4. The method of claim 2 wherein said bioactive material causes the interconversion of Nicotinamide Adenine Dinucleotide Phosphate, NAD(P), with its reduced form, NAD(P)H, and said method comprises determining said bioactive material by measuring NAD(P)H.

5. The method of claim 1 wherein said light energy is transmitted in the range of ultraviolet wavelengths bordering on the spectrum of visible light.

6. The method of claim 5 wherein said light energy is transmitted at a wavelength of about 320 m$\mu$.

7. The method of claim 1 wherein said bioactive materials absorb light at different wavelengths.

8. The method of claim 1 wherein said bioactive material causes the interconversion of Nicotinamide Adenine Dinucleotide Phosphate, NAD(P), with its reduced form, NAD(P)H, and said method comprises determining said bioactive material by measuring NAD(P)H.

9. The method of claim 8 wherein said light energy is transmitted in the range of ultraviolet wavelengths bordering on the spectrum of visible light.

10. The method of claim 8 wherein said light energy is transmitted at a wavelength of about 320 m$\mu$.

* * * * *